United States Patent [19]

Borthwick et al.

[11] Patent Number: 4,857,531
[45] Date of Patent: Aug. 15, 1989

[54] GUANINE DERIVATIVES

[75] Inventors: David A. Borthwick, London; Barrie E. Kirk, Ickenham; Derek N. Evans, Greenford; Keith Biggadike, Northolt; Leslie Stephenson, Coddenham near Ipswich, all of England

[73] Assignee: Glaxo Group Limited, London, England

[21] Appl. No.: 896,957

[22] Filed: Aug. 15, 1986

[30] Foreign Application Priority Data

Aug. 16, 1985 [GB] United Kingdom ............... 8520553
Jun. 13, 1986 [GB] United Kingdom ............... 8614395

[51] Int. Cl.$^4$ .................. C07D 473/18; A61K 31/52
[52] U.S. Cl. ............................. 514/262; 544/276; 544/244
[58] Field of Search .................. 544/276, 277, 244; 514/262

[56] References Cited

U.S. PATENT DOCUMENTS

| | | | |
|---|---|---|---|
| 4,543,255 | 9/1985 | Shealy et al. | 514/258 |
| 4,605,659 | 8/1986 | Verbeyden et al. | 514/262 |
| 4,714,701 | 12/1987 | Beauchamp | 544/276 |
| 4,728,736 | 3/1988 | Shealy et al. | 544/254 |

OTHER PUBLICATIONS

H. Lee and R. Vince, *J. Pharm. Sci.*, 1980, 69, 1019–1021.
M. Ikehara and J. Imura, *Chem. Pharm. Bull.*, 1981, 29, 1034–1038.

*Primary Examiner*—Nicholas S. Rizzo
*Attorney, Agent, or Firm*—Bacon & Thomas

[57] ABSTRACT

The present invention provides a compound of formula (I)

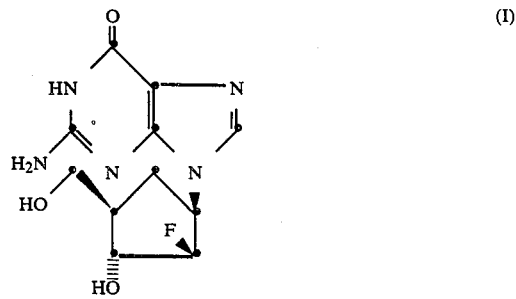

and salts and solvates thereof, and describes processes for their preparation, pharmaceutical compositions containing them and their use in the treatment of viral diseases, especially those caused by the Herpetoviridae.

9 Claims, No Drawings

GUANINE DERIVATIVES

This invention relates to new guanine derivatives, to processes for their preparation, to pharmaceutical compositions containing them and to their use in medicine.

Existing treatments for viral infections include the administration of nucleoside analogues such as 2'-deoxy-5-iodouridine, 9-(2-hydroxyethoxymethyl)guanine and 9-β-D-arabinofuranosyladenine. Carbocyclic analogues of nucleosides are also known to have an effect against certain viruses, and in UK Patent Specification No. 2129425A and J. Med. Chem. 1984, 27, 1416–1421 such compounds are disclosed having activity against strains of herpes simplex I and II. There is however a need for compounds with better antiviral activity that also are less cytotoxic.

We have now found that the new fluoro substituted guanine derivative of formula (I) below has improved activity against viruses, especially Herpetoviridae, whilst having a low level of cytotoxicity.

Thus, according to one aspect, the invention provides a compound of formula (I)

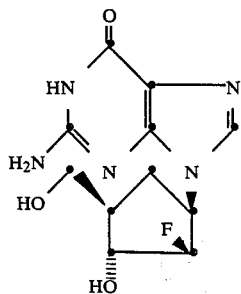

and salts and solvates thereof.

It will be appreciated that, for pharmaceutical use, the salts referred to above will be the physiologically acceptable salts, but other salts may find use, for example in the preparation of compounds of formula (I) and the physiologically acceptable salts thereof.

Suitable physiologically acceptable salts of the compound of formula (I) include acid addition salts formed with organic or inorganic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, glutaconates, acetates, tricarballylates, citrates, fumarates and maleates) and inorganic base salts such as alkali metal salts (for example sodium salts).

The compound of formula (I) may exist in tautomeric forms, for example in the form

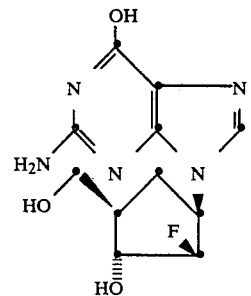

and it will be understood that all tautomeric forms of the compound of formula (I) are included within the scope of the invention.

It is to be understood that the present invention encompasses the individual enantiomers of the compound of formula (I) and its tautomers as well as wholly or partially racemic mixtures of such enantiomers, even though the precise structures as set out only relate to one enantiomer.

It will be further understood that the invention includes within its scope biological precursors of the compound of formula (I) and its physiologically acceptable salts with acids and bases. Biological precursors include for example metabolically labile esters which are converted in vivo into the parent compound.

Particularly preferred, according to the invention, are (±)(1'α,2'α,3'β,4'α)-2-amino-1,9-dihydro-9-[2-fluoro-3-hydroxy-4-(hydroxymethyl)cyclopentyl]-6H-purin-6-one and its physiologically acceptable salts and solvates; and (+)(1'R,2'R,3'R,4'R)-2-amino-1,9-dihydro-9-[2-fluoro-3-hydroxy-4-(hydroxymethyl)cyclopentyl]-6H-purin-6-one and its physiologically acceptable salts and solvates.

We have found that the compound of formula (I) is highly potent in vitro and in vivo against strains of both herpes simplex virus type I and herpes simplex virus type II whilst having a low level of cytotoxicity. We have also found the compound of formula (I) to be active in vitro against human cytomegalovirus and varicella zoster virus.

In vitro testing was carried out using the standard plaque reduction test whilst in vivo testing was carried out on the mouse according to the method described by Ericson et al. (1985) Antimicrobial Agents-Chemotherapy 27, 753–759.

It should be noted that the compound of formula (I) lacks a glycosidic bond which forms a site for both chemical and biological cleavage. Stability against glycosidic cleavage is, of course, a valuable feature in compounds for in vivo use.

In view of their antiviral activity, the compound according to the invention and its physiologically acceptable salts recommend themselves for the treatment of a variety of diseases caused by viruses, particularly primary and recurrent infections caused by the Herpetoviridae in human beings and animals. Such diseases include stomatitis, skin eruptions, shingles, encephalitis, eye and genital herpes infections, retinitis and pneumonitis.

The invention accordingly provides a compound of formula (I) and its physiologically acceptable salts for use in the therapy or prophylaxis of viral infections, especially Herpetoviridae (e.g. herpes simplex) infections, in a human or animal subject.

The compound according to the invention may be formulated for administration in any convenient way, and the invention therefore also includes within its scope pharmaceutical compositions comprising a compound of formula (I) or a physiologically acceptable salt thereof adapted for use in human or veterinary medicine. Such compositions may be presented for use in conventional manner in admixture with one or more physiologically acceptable carriers or excipients. The compositions may optionally further contain one or more other therapeutic agents which may if desired be a different antiviral agent.

Thus, the compound according to the invention may be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example lactose, sugar, maize-starch, calcium phosphate or sorbitol; lubricants, for example magnesium stearate, talc, polyethylene glycol or silica; disintegrants, for example potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose/sugar syrup, gelatin, hydroxymethyl cellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The compound may also be formulated as suppositories, e.g. containing conventional suppository bases such as cocoa butter or other glycerides.

For buccal administration the compositions may take the form of tablets or lozenges formulated in conventional manner.

The compound according to the invention may also be formulated for injection and may be presented in unit dose form in ampoules or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

For topical administration the compound according to the invention may be formulated as ointments, creams, lotions, powders, pessaries, sprays, aerosols or drops (e.g. eye or nose drops). Ointments and creams may, for example, be formulated with an aqueous or oily base with the addition of suitable thickening and/or gelling agents. Such bases may thus, for example, include water and/or an oil such as liquid paraffin or a vegetable oil such as arachis oil or castor oil. Thickening agents which may be used include soft paraffin, aluminium stearate, cetostearyl alcohol, polyethylene glycols, hydrogenated lanolins and beeswax.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base, for example talc, lactose or starch. Drops may be formulated with an aqueous or non-aqueous base also comprising one or more dispersing agents, solubilising agents or suspending agents.

Aerosol sprays are conveniently delivered from pressurized packs, with the use of a suitable propellant, e.g. dichlorodifluoromethane, trichlorofluoromethane, dichlorotetrafluoroethane, carbon dioxide or other suitable gas.

The pharmaceutical compositions according to the invention may also contain other active ingredients such as antimicrobial agents, or preservatives.

The compositions may contain from 0.1%–99% of the active material. For topical administration, for example, the composition will generally contain from 0.01% to 20%, more preferably 0.5% to 5% of the active material.

For topical administration the daily dosage as employed for adult human treatment will range from 0.1 mg to 1000 mg, preferably 0.5 mg to 10 mg. However, it will be appreciated that extensive skin infections may require the use of higher doses.

For systemic administration the daily dosage as employed for adult human treatment will range from 5 mg to 5000 mg, preferably 50 mg to 2000 mg, which may be administered in 1 to 5 daily doses, for example, depending on the route of administration and the condition of the patient. When the compositions comprise dosage units, each unit will preferably contain 2 mg to 2000 mg of active ingredient, for example 50 mg to 500 mg. For serious infections the compound may be administered by intravenous infusion using, for example 0.01 to 10 mg/kg/hr of the active ingredient.

According to another aspect of the invention we provide processes for the preparation of a compound of formula (I). Thus one process (A) for the preparation of a compound of formula (I) comprises the step of converting the atom or group X in a compound of formula (II)

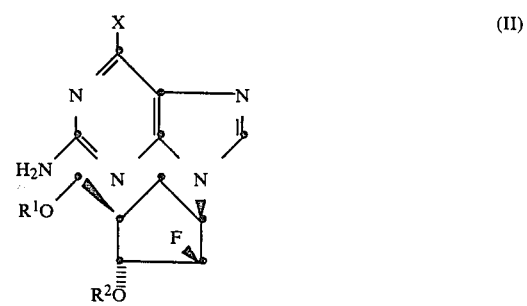

(II)

(wherein X represents an atom or a group convertible into a hydroxy group and $R^1$ and $R^2$, which may be the same or different, represent hydrogen atoms or protecting groups) or a salt thereof, into a hydroxy group, followed where necessary by the removal of any protecting groups.

The atom or group X may be, for example, an atom or group convertible by hydrolysis into a hydroxy group, such as halogen atom, e.g. chlorine.

It will be appreciated that the resulting compound in which X is a hydroxy group is merely the tautomeric form of the compound of formula (I).

The hydrolysis reaction may be effected in an aqueous solvent such as water or a mixture of water and a water-miscible solvent such as an alcohol, e.g. methanol or ethanol, dioxan, tetrahydrofuran, a ketone, e.g. acetone, an amide, e.g. dimethylformamide or a sulphoxide, e.g. dimethylsulphoxide, conveniently in the presence of an acid or base.

Suitable acids which may be used in the above process according to the invention include organic acids, e.g. p-toluenesulphonic acid, and inorganic acids, e.g. hydrochloric acid, nitric acid and sulphuric acid. In some cases the acid may also be used as the reaction solvent.

Suitable bases which may be used in the above process according to the invention include inorganic bases, e.g. alkali metal hydroxides, or carbonates such as sodium or potassium hydroxide or carbonate.

The process is conveniently effected at a temperature in the range of $-10°$ to $+150°$ C., e.g. $50°$ to $120°$ C.

Where $R^1$ and/or $R^2$ represents a protecting group, it may be any conventional hydroxyl protecting group, for example as described in 'Protective Groups in Organic Chemistry', Ed. J. F. W. McOmie (Plenum Press; 1973) or 'Protective Groups in Organic Synthesis' by Theodora W. Greene (John Wiley and Sons, 1981). Examples of suitable protecting groups include alkyl groups such as methoxymethyl; aralkyl groups such as benzyl, diphenylmethyl or triphenylmethyl; heterocyclic groups such as tetrahydropyranyl; acyl groups such as acetyl; and silyl groups such as trialkylsilyl groups, e.g. t-butyldimethylsilyl. $R^1$ and $R^2$ may also form a single protecting group, for example a tetraalkyldisilyloxy group such as 1,1,3,3-tetraisopropyldisilyloxy or a benzylidene group.

The protecting groups may be removed by using conventional techniques to yield a compound of formula (I). Thus an alkyl, aryl, silyl or heterocyclic group may, for example, be removed by solvolysis, e.g. hydrolysis under acidic or basic conditions, and an aralkyl group may be cleaved with a boron trihalide e.g. boron trichloride in a solvent such as methylene chloride and at low temperature. Where $R^1$ and $R^2$ together represent a tetraalkyldisilyloxy group, this may be removed by treatment with a tetraalkylammonium halide, e.g. tetra-n-butylammonium fluoride.

Another process (B) for the preparation of a compound of formula (I) comprises reacting a compound of formula (III)

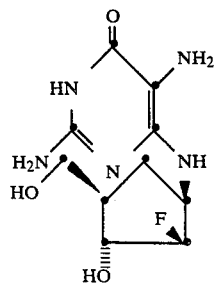

(III)

(or a salt or a protected derivative thereof) with formic acid or a reactive formic acid derivative such as trialkyl orthoformate, e.g. triethyl orthoformate; a dialkoxymethyl acetate, e.g. diethoxymethyl acetate; dithioformic acid; formamide; or sym triazine.

The reaction is conveniently effected in a suitable solvent such as an amide, e.g. dimethylformamide or dimethylacetamide, a chlorinated hydrocarbon, e.g. methylene chloride, an ether, e.g. tetrahydrofuran or a nitrile, e.g. acetonitrile. In some cases the reaction may conveniently be effected in the presence of a catalyst such as a strong acid, e.g. concentrated hydrochloric, nitric or sulphuric acid. The reaction may be effected at a temperature in the range of $-25°$ to $+150°$ C., e.g. $0°$ to $100°$ C.

The intermediate compounds of formula (II) may be prepared by reacting a compound of formula (IV)

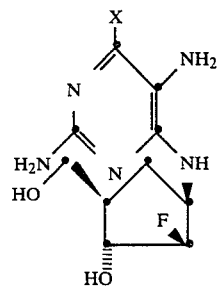

(IV)

(wherein X is as defined previously) or a salt or a protected derivative thereof with formic acid or a reactive formic acid derivative according to the method of process (B) above.

If desired, the product of the above reaction may be used directly in process (A) according to the invention to prepare the compound of formula (I), i.e. without isolation of the compound of formula (II).

The compounds of formulae (III) and (IV) may be prepared by reducing the appropriate compound of formula (V)

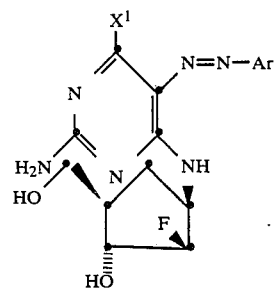

(V)

(wherein $X^1$ represents a hydroxy group or the group X as defined previously and Ar represents an aromatic group, e.g. p-chlorophenyl) or a salt or a protected derivative thereof.

Suitable reducing agents include, for example, a reducing metal such as zinc in the presence of an acid, e.g. acetic acid; or zinc in the presence of ammonium chloride in an alcohol such as methanol or ethanol; stannous chloride; a dithionite, e.g. sodium dithionite; borane; and hydrogen in the presence of a catalyst such as palladium on charcoal. It will be appreciated that the choice of reducing agent will depend on the nature of the group $X^1$.

The compounds of formula (V) may be prepared by reacting a compound of formula (VI)

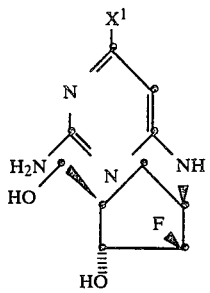 (VI)

(wherein $X^1$ is as defined previously) or a salt or a protected derivative thereof with a diazonium salt of formula (VII)

 (VII)

(wherein Ar represents an aromatic group e.g. p-chlorophenyl and E represents an anion e.g. a halide ion such as chloride).

The reaction may be effected in a solvent such as water, an organic acid such as acetic acid or mixtures thereof, conveniently at around ambient temperatures, e.g. $-10°$ to $+30°$ C.

The compounds of formula (VI) may be prepared by reacting the compound of formula (VIII)

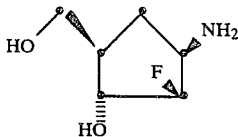 (VIII)

or a salt or a protected derivative thereof with a pyrimidine of formula (IX)

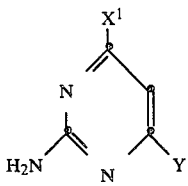 (IX)

(wherein $X^1$ is as defined previously and Y represents a leaving atom or group, for example a halogen atom, e.g. chlorine) or a salt or a protected derivative thereof.

The reaction is conveniently effected in a suitable solvent such as an alcohol, e.g. ethanol, 2-propanol or 1-butanol, and in the presence of a base, desirably a non-nucleophilic base, e.g. a tertiary amine such as triethylamine. The reaction may be effected at a temperature in the range of 25° to 150° C.

The compounds of formula (VIII) may be prepared by deprotecting a compound of formula (X)

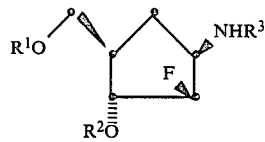 (X)

(wherein $R^1$, $R^2$ and $R^3$, which may be the same or different, each represents a hydrogen atom or a protecting group with the proviso that at least one of $R^1$, $R^2$ and $R^3$ represents a protecting group) or a salt thereof.

The protecting group represented by $R^3$ may be a conventional protecting group as described above. A protecting group which we have found may conveniently be used is the 2,4-dinitrophenyl group. This group may be removed by treatment with a base e.g. sodium hydroxide or a basic ion exchange resin.

The compounds of formula (X) may be prepared by reacting a compound of formula (XI)

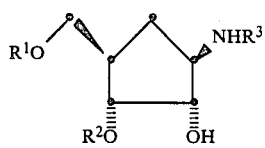 (XI)

(wherein $R^1$, $R^2$ and $R^3$ are as defined previously) with a fluorinating agent.

Suitable fluorinating agents include diethylaminosulphur trifluoride (DASI) or diethyl-(2-chloro-1,1,2-trifluoroethyl)amine. The reaction is conveniently effected in an inert solvent such as a halogenated hydrocarbon, e.g. methylene chloride or chloroform, or an ether, e.g. tetrahydrofuran, and at a temperature of, for example, from $-70°$ to $0°$ C. Alternatively the reaction may be effected using hydrogen fluoride in pyridine or triethylamine.

The compounds of formula (XI) may be prepared by protecting the compound of formula (XII)

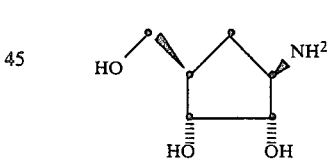 (XII)

or a salt thereof.

The protecting groups may be introduced in conventional manner. Thus, for example, a dinitrophenyl group $R^3$ may be introduced by reacting the compound of formula (XII) with 2,4-dinitrofluorobenzene in the presence of a base, e.g. sodium carbonate.

A tetraalkyldisilyloxy group represented by $R^1$ and $R^2$ may be introduced by reaction with a 1,3-dihalo-1,1,3,3-tetraalkyldisiloxane, e.g. 1,3-dichloro-1,1,3,3-tetraisopropyldisiloxane, conveniently in the presence of a base e.g. an organic base such as imidazole.

The compound of formula (XII) is a known compound. It may be prepared according to the method described by R. C. Cermak and R. Vince in *Tetrahedron Lett.*, 1981, 22, 2331.

The compounds of formulae (V) and (VI) wherein $X^1$ represents a hydroxy group may additionally be prepared from the corresponding compounds where $X^1$ represents a group convertible into a hydroxy group according to the method of process (A) above.

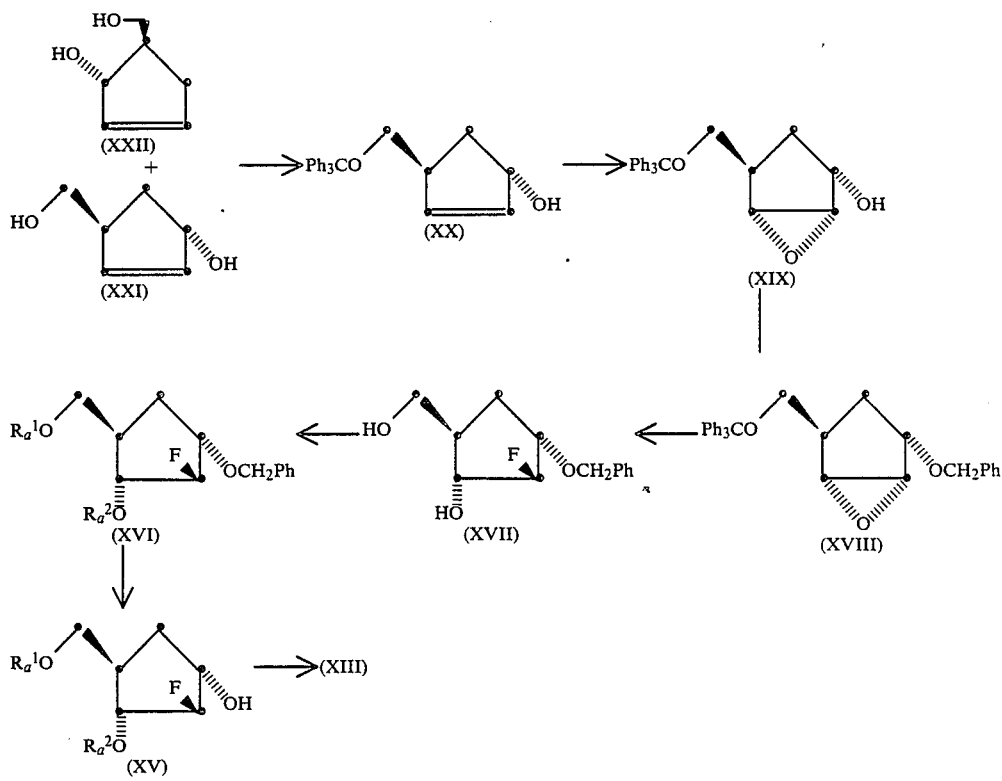

The compounds of formula (II) may also be prepared by reacting compounds of formula (XIII)

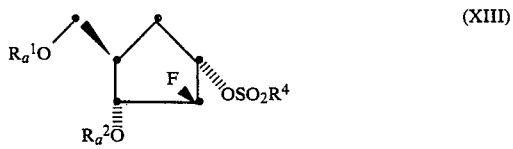

[wherein $R_a^1$ and $R_a^2$ are conventional hydroxy protecting groups as described above, e.g. methoxymethyl, and $R^4$ is an alkyl (e.g. methyl), haloalkyl (e.g. trifluoromethyl) or aryl (e.g. tolyl) group] with a purine derivative (XIV)

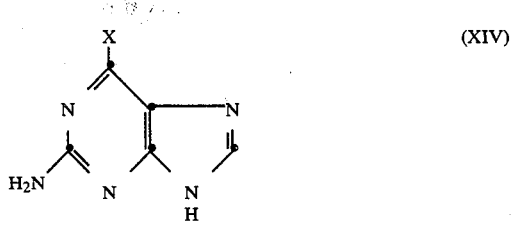

(wherein X is as defined previously) or a salt or a protected derivative thereof.

The reaction is conveniently effected in a suitable solvent e.g. dimethylsulphoxide, and in the presence of a base such as an alkali metal carbonate, e.g. potassium carbonate. The reaction may, for example, be effected at a temperature in the range of 25° to 150 ° C.

The compounds of formula (XIII) may, for example, be prepared by the following reaction sequence from a mixture of the known cyclopentene derivatives (XXI) and (XXII):

Thus, a mixture of the compounds of formulae (XXI) and (XXII) is selectively tritylated to give, after separation by silica gel chromatography, a compound of formula (XX). This compound is oxidised using a suitable peroxide oxidising agent such as tert-butyl hydroperoxide in the presence of a vanadium catalyst (e.g. vanadyl acetylacetonate) to give the epoxide of formula (XIX). The compound of formula (XIX) is benzylated under standard conditions to give the compound of formula (XVIII), and this compound is treated with a suitable fluorinating agent such as potassium hydrogen difluoride to give, as a result of concomitant detritylation, the compound of formula (XVII). The fluorination reaction takes place in the presence of a solvent such as an alcohol, e.g., ethylene glycol, at elevated temperatures e.g. 100° to 200° C. Introduction of suitable protecting groups in a conventional manner provides the compounds of formula (XVI). Thus, for example, a pair of methoxymethyl protecting groups may be introduced by reacting the compound of formula (XVII) with chloromethyl methyl ether in a halogenated hydrocarbon solvent such as dichloromethane, conveniently at room temperature. Preferably, the reaction is effected in the presence of a base, desirably a non-nucleophilic base, e.g. a tertiary amine such as diisopropylethylamine. The benzyl group in the compound of formula (XVI) is cleaved by standard hydrogenolysis to give a compound of formula (XV) which upon sulphonation with a suitable sulphonyl halide $R^4SO_2Hal$ (wherein $R^4$ is as defined previously and Hal is a halogen atom e.g. chlorine) provides the desired intermediate of formula (XIII).

The mixture of compounds of formulae (XXI) and (XXII) may be prepared according to the methods described by H. Paulsen and U. Maass in *Chem. Ber.* 1981, 114, 346.

Another process (C) for the preparation of a compound of formula (I) comprises cyclising a compound of formula (XXIII)

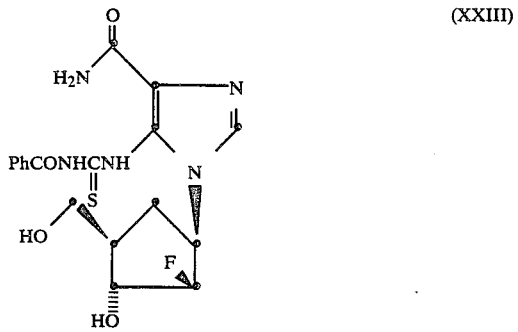

(XXIII)

or a salt or a protected derivative thereof, followed, where necessary, by the removal of any protecting groups. The reaction is conveniently effected in two steps. the first step involves treating the compound of formula (XXIII) with an alkylating agent such as an alkyl halide (e.g. methyl iodide), preferably in the presence of a suitable base. Suitable bases include alkali metal hydroxides (e.g. sodium or potassium hydroxide), alkali metal carbonates and alkali metal bicarbonates. This reaction is conveniently carried out at room temperature. The second step involves treating the product of the first step with ammonia in a suitable polar aprotic solvent such as an amide (e.g. dimethylformamide) or a sulphoxide (e.g. dimethylsulphoxide) or, alternatively, an aqueous ammonia solution may be used. This reaction is conveniently effected at a temperature in the range of from 20° to 130° C., e.g. reflux.

The compound of formula (XXIII) may be prepared from a compound of formula (XXIV)

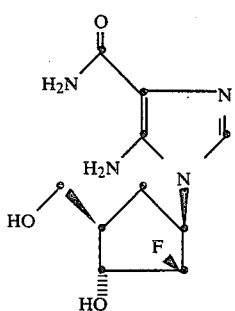

(XXIV)

or a salt or a protected derivative thereof, by reaction with benzoyl isothiocyanate in an alcohol solvent (e.g. ethanol or n-butanol) conveniently at an elevated temperature e.g. reflux.

The compound of formula (XXIV) may be prepared from a compound of formula (VIII), or a salt (e.g. the hydrochloride) or a protected derivative thereof, by reaction with an alkyl N-(carbamoylcyanomethyl)formimidate e.g. ethyl N-(carbamoylcyanomethyl)formimidate [EtOCH=NCH(CN)CONH$_2$]. The reaction is effected in a suitable solvent e.g. acetonitrile in the presence of a base, for instance an organic base such as an amine (e.g. triethylamine), conveniently at an elevated temperature e.g. reflux.

Compounds of formulae (II) to (VI), (VIII), (X), (XI), (XIII), (XV) to (XX), (XXIII) and (XXIV) are all novel intermediates and form further features of the invention.

Compounds of formulae (VIII) and (XV) are key intermediates in the synthesis of the compound of the invention.

When a specific enantiomer of formula (I) is required, this may be prepared for example by resolution of the corresponding racemate of formula (I). Thus, according to one method (based on that of Herdewijn et al., J. Med. Chem., 1985, 28, 1385–1386, and described in full in Example 2 hereinafter), phosphorylation of the racemate of formula (I) yields a mixture containing the 4-hydroxymethyl monophosphate of each of the enantiomers of formula (I), which is then subjected to selective enzymic degradation using 5'-nucleotidase to give a mixture containing the (+) enantiomer of formula (I) and the unreacted monophosphate of the (−) enantiomer. Separation of the mixture by e.g. reverse phase hplc yields the desired (+) enantiomer and the remaining monophosphate which may then be treated with alkaline phosphatase to yield the (−) enantiomer of formula (I). It is anticipated that further methods of resolution known per se could also be used to isolate the individual enantiomers.

The 4-hydroxymethyl monophosphates of the (+) and (−) enantiomers of the compound of formula (I) are novel intermediates and constitute a further aspect of the invention.

When it is desired to prepare an acid addition salt of a compound of formula (I) the product of any of the above procedures may be converted into a salt by treatment of the resulting free base with a suitable acid using conventional methods.

Physiologically acceptable acid addition salts of the compound of formula (I) may be prepared by reacting a compound of formula (I) in the form of the free base with an appropriate acid optionally in the presence of a suitable solvent such as an ester (e.g. ethyl acetate) or an alcohol (e.g. methanol, ethanol or isopropanol).

Inorganic basic salts may be prepared by reacting the free base of a compound of formula (I) with a suitable base e.g. an alkoxide such as sodium methoxide optionally in the presence of a solvent (e.g. an alcohol such as methanol).

Physiologically acceptable salts may also be prepared from other salts, including other physiologically acceptable salts, of the compound of formula (I) using conventional methods.

The following Preparations and Examples illustrate the invention. All temperatures are in 20° C.

INTERMEDIATE 1

(±)(1β,2β,3α,5α)-5-[(2,4-Dinitrophenyl)amino]-3-hydroxymethyl-1,2-cyclopentanediol (±)(1β,2β,3α,5α)-5-Amino-3-hydroxymethyl-1,2-cyclopentanediol (prepared according to the method described in R. C. Cermak and R. Vince, *Tetrahedron Lett.*, 1981, 22, 2331) (1.84 g), anhydrous sodium carbonate (4.2 g) and 2,4-dinitrofluorobenzene (1.7 g) were stirred at room temperature in N,N-dimethylformamide (15 ml) for 18 hours. The mixture was diluted with chloroform (ca 300 ml) and passed down a column of silica gel (300 g) made up in chloroform. The column was eluted with chloroform-methanol mixtures. Eluate containing the product was combined and the solvent was evaporated under reduced pressure to give the *title*

*compound* as a solid (2.62 g)., $\lambda_{max}{}^{H2O}$ 265 nm ($E_1{}^1$ 255), 361.5 nm ($E_1{}^1$ 527).

INTERMEDIATE 2

(±)(8α,9β)-8-[(2,4-Dinitrophenyl)amino]-hexahydro-9-hydroxy-2,2,4,4-tetrakis(1-methylethyl)cyclopenta(f)-1,3,5,2,4-trioxadisilocin Intermediate 1 (1.2 g) was dissolved in N,N-dimethylformamide (10 ml) and imidazole (1.04 g) was added. The mixture was stirred and 1,3-dichloro-1,1,3,3-tetraisopropyldisiloxane (1.33 g) was added. When the addition was complete the solution was allowed to stand at room temperature for 3 hours. The mixture was poured into water and extracted with ethyl acetate. The combined organic extracts were dried (MgSO$_4$) and the solvent was removed under reduced pressure to give an oil. This was chromatographed on a silica gel (125 g) column eluting with petrol:ethyl acetate mixtures to afford the *title compound* as a crystalline solid (1.55 g), $\lambda_{max}{}^{CHCl3}$ 263 nm ($E_1{}^1$ 143), $\lambda_{max}$ 346.5 nm ($E_1{}^1$ 277), $\nu_{max}$ 3650, 3530, 3360, 1615, 1588, 1518 and 1330 cm$^{-1}$.

INTERMEDIATE 3

(±)(8α,9α)-8-[(2,4-Dinitrophenyl)amino]-9-fluoro-hexahydro-2,2,4,4-tetrakis(1-methylethyl)cyclopenta(f)-1,3,5,2,4-trioxadisilocin A solution of Intermediate 2 (700 mg) in dry dichloromethane (20 ml) was added slowly over 30 minutes to a solution of diethylaminosulphur trifluoride (409 mg) in dry dichloromethane (20 ml) at −78°. The reaction mixture was allowed to attain room temperature and was then cooled to −78° and poured onto ice/solid sodium bicarbonate. The mixture was allowed to attain room temperature and the aqueous phase was separated and washed with dichloromethane. The organic phases were combined and dried (Na$_2$SO$_4$) and the solvent was evaporated under reduced pressure to give a solid (660 mg). This was chromatographed down a silica gel (40 g) column which was eluted with hexane:ethyl acetate mixtures. Eluate containing product was combined and the solvent was evaporated under reduced pressure to give a solid (350 mg). A portion (280 mg) of this material was recrystallised from ethanol to give the *title compound* as a crystalline solid (193 mg), m.p. 134°-136°.

INTERMEDIATE 4

(±)(1α,2β,3α,4α)-4-Amino-3-fluoro-2-hydroxycyclopentanemethanol

A solution of Intermediate 3 (3 g) in tetrahydrofuran (100 ml) was treated with tetrabutylammonium fluoride (1.307 g) in tetrahydrofuran (5 ml). The resulting solution was allowed to stand at room temperature for 2 hours and the solvent was then removed under reduced pressure. The residue was partitioned between ethyl acetate and water and the organic phase was separated, washed with water and 2N hydrochloric acid. The aqueous phases were combined and back extracted with ethyl acetate. The organic phases were combined, dried (MgSO$_4$) and the solvent was evaporated under reduced pressure to give a two phase system of a dark brown oil and a colourless opaque oil. This was treated with methanol and the dark brown solution was decanted from the colourless oil which was discarded. The methanol solution was evaporated under reduced pressure to give an oil (3.1 g). The oil was dissolved in acetone:water (2:1, 75 ml) and the resulting solution was treated with Dowex-2 resin [OH— form] (70 g). The mixture was stirred at room temperature for 4 hours and the resin was then removed by filtration and washed with water. The washings and filtrate were combined and concentrated under reduced pressure. 2N Hydrochloric acid was added and the solution was partitioned with ethyl acetate. The aqueous phase was evaporated under reduced pressure to give an oil (790 mg) which was dissolved in methanol and stirred in the presence of charcoal for 3 hours. Removal of the charcoal by filtration through Kieselguhr gave a solution which was passed down an Amberlite IR 400 (OH— form) ion exchange resin using methanol as the eluant. Eluate which contained the product was combined and the solvent was evaporated under reduced pressure to give the *title compound* as an oil (474 mg), $\nu_{max}{}^{Nujol}$ 3300 and 1595 cm$^{-1}$. $^1$H n.m.r. (DMSO-d$_6$) δ4.41 (1H), 4.14 (1H), 3.82 (1H), 3.3–3.5 (2H), 3.21 (1H), 2.4–2.6 (2H), 1.94 (1H), 1.76 (1H) and 1.12 (1H).

INTERMEDIATE 5

(±)(1α,2β,3α,4α)-4-[[2-Amino-4-chloro-5-[(4-chlorophenyl)-azo]-6-pyrimidinyl]amino]-3-fluoro-2-hydroxycyclopentanemethanol Intermediate 4 (462 mg), and its hydrochloride salt (450 mg), triethylamine (3.848 g) and 2-amino-4,6-dichloropyrimidine (1.307 g) in n-butanol (30 ml) were stirred and heated under reflux under an atmosphere of nitrogen for 3 days. The solvent was removed under reduced pressure and the residue was dissolved in water and partitioned with dichloromethane. The aqueous phase was stirred briefly with Dowex-2 ion-exchange resin [OH— form] (20 ml). After removal of the resin by filtration the aqueous solution was evaporated to dryness under reduced pressure and the residue was azeotroped with ethanol. It was then passed down a silica gel column which was eluted with 4:1 chloroform:methanol. Eluate which contained the product together with a more polar impurity were combined and the solvent was removed under reduced pressure to give a solid (1.284 g). This was dissolved in water (24 ml) and glacial acetic acid (24 ml) and sodium acetate trihydrate (10.1 g) was added. The resulting solution was stirred at room temperature and an ice-cold solution of p-chlorobenzenediazonium chloride (prepared by the addition of a sodium nitrite (390 mg) solution in water (3 ml) to a solution of p-chloroaniline (683 mg) in water (9 ml) and 12N hydrochloric acid (3 ml) at 0°–5°) was added dropwise to the stirred solution. When the addition was complete the mixture was stirred at room temperature for 18 hours. The mixture was cooled in ice and the resulting yellow precipitate was collected by filtration, washed with water and dried in vacuo to give a solid (960 mg). This was recrystallised from methanol to give the *title compound* as a solid, m.p. 258°–262° (Kofler).

INTERMEDIATE 6

(±)(1α,2β,3α,4α)-4-[(2,5-Diamino-4-chloro-6-pyrimidinyl)amino]-3-fluoro-2-hydroxycyclopentanemethanol Intermediate 5 (778 mg) was suspended in ethanol (20 ml), glacial acetic acid (1.5 ml) and water (20 ml). The mixture was stirred vigorously and heated under reflux under an atmosphere of nitrogen. Zinc dust (1.24 g) was added in small portions over 30 minutes and the mixture was then heated under reflux, with vigorous stirring, for a further 75 minutes. Excess zinc was removed by filtration and was washed with ethanol. The washings and filtrate were combined and the solvent was evaporated under reduced pressure to give a brown residue. This was dissolved in water and was partitioned with dichloromethane. The aqueous phase was evaporated under reduced pressure and the residue was chromatographed on a silica gel column which was eluted with 4:1 chloroform:methanol. Eluate which contained the product was combined and the solvent was removed under reduced pressure to give the *title compound* as a solid (336 mg), m.p. 165°–166°.

INTERMEDIATE 7

(±)(1β,4α)-4-[((Triphenylmethyl)oxy)methyl]-2-cyclopenten-1-ol

A mixture of (±)(1α,4β)-4-hydroxy-2-cyclopentene-1-methanol[1] and (±)(1α,2β)-2-hydroxy-3-cyclopentene-1-methanol[1] (10.42 g) was dissolved in pyridine (123 ml) and the solution was stirred and treated with triphenylmethyl chloride (28.03 g). The mixture was stirred at room temperature for 72 hours and was then poured into ice/water (250 ml) and partitioned with ethyl acetate (350 ml). The organic phase was separated and the aqueous phase was re-extracted with ethyl acetate (350 ml). The organic extracts were combined, washed with 1N hydrochloric acid (250 ml), water (250 ml) and saturated sodium bicarbonate solution. The organic phase was dried (MgSO$_4$) and evaporated under reduced pressure to give a yellow oil (32.81 g). This was subjected to silica gel (Merck Kieselgel 60, Mesh 240–400) chromatography using toluene:ethyl acetate (12:1) as the eluting solvent. Fractions which contained the most polar component were combined and the solvent was evaporated under reduced pressure to give the *title compound* as an opaque yellow oil (7.12 g). Crystallisation from 40°–60° petroleum ether/isopropyl ether gave the *title compound* as a colourless solid m.p. 83°, $v_{max}$ 3230 cm$^{-1}$.

1. H. Paulsen & U. Maass, *Chem. Ber.*, 1981, 114, 346.

INTERMEDIATE 8

(±)(1α,2β,4α,5α)-4-[((Triphenylmethyl)oxy)methyl]-6-oxabicyclo[3.1.0]hexan-2-ol

Intermediate 7 (6.95 g) and vanadyl acetylacetonate (54 mg) were stirred in toluene (70 ml) and treated dropwise with tert:butyl hydroperoxide (8.13 ml, 3M solution in toluene). When the addition was complete the mixture was stirred at room temperature for 21 hours. Aqueous sodium sulphite solution (40 ml) was added and the mixture was stirred at room temperature for 2 hours. The organic phase was separated and washed twice with water (100 ml). The combined aqueous phases were extracted with toluene (100 ml) and the combined organic phases were dried (MgSO$_4$) and evaporated under reduced pressure to give the *title compound* as a yellow oil. $^1$H n.m.r. (CDCl$_3$) δ1.37(1H), 1.79(1H), 1.58(1H), 2.59(1H), 3.00(1H), 3.19(1H), 3.50(1H), 3.55(1H), 4.40(1H), 7.2–7.56(15H).

INTERMEDIATE 9

(±)(1α,2β,4α,5α)-4-Phenylmethoxy-2-[((triphenylmethyl)oxy)methyl]-6-oxabicyclo[3.1.0]hexane Intermediate 8 (139 mg) was dissolved in dry tetrahydrofuran (3 ml) and the solution was added dropwise at 0° to a stirred suspension of sodium hydride (60%, 16.7 mg) in dry tetrahydrofuran (5 ml) under nitrogen. When the addition was complete the mixture was stirred at room temperature for 2 hours and benzyl bromide (70 mg) and tetrabutylammonium iodide (5 mg) were then added. The mixture was stirred at room temperature, under nitrogen, for 18 hours and was then poured into water and partitioned with ethyl acetate. The organic phase was separated, washed with water and dried (MgSO$_4$). Evaporation of the solvent under reduced pressure gave a brown oil (223 mg) which was subjected to preparative layer chromatography (Whatman PK6F plates) using 4:1 hexane:ethyl acetate as the developing solvent. The major component was eluted from the plates with ethyl acetate to give, after evaporation of the solvent under reduced pressure, the *title compound* as a colourless opaque glass (128 mg), $^1$H n.m.r. (CDCl$_3$) δ1.46–1.68(2H), 2.54(1H), 2.96(1H) 3.13(1H), 3.42(1H), 3.51(1H), 6.15(1H), 6.58(2H), 7.18–7.48(20H).

INTERMEDIATE 10

(±)(1α,2β,3α,4β)-3-Fluoro-2-hydroxy-4-phenylmethoxycyclopentanemethanol

Intermediate 9 (300 mg) and potassium hydrogen difluoride (300 mg) were suspended in redistilled ethylene glycol (5 ml). The mixture was stirred and heated at 150°–160° for 5 hours and was then stood overnight at room temperature. The mixture was purified by silica gel chromatography (Merck Kieselgel 60, 70–240 Mesh) using hexane-ethyl acetate mixtures as the eluting solvent. Fractions which contained the most polar component (not baseline) were combined and the solvent was evaporated under reduced pressure to give the *title compound* as a pale brown oil, $v_{max}^{CHBr}$3580, 3450 cm$^{-1}$. $^1$H n.m.r. (CDCl$_3$) δ1.5–2.0(2H), 2.28(1H), 2.60(1H), 3.63(1H), 3.79(1H) 3.92–4.14(2H), 4.54(1H), 4.63(1H), 4.87(1H), 7.23–7.40(5H).

INTERMEDIATE 11

(±)(1β,2α,3β,4α)-2-Fluoro-3-(methoxymethoxy)-4-[(methoxymethoxy)methyl]-1-phenylmethoxycyclopentane Intermediate 10 (956 mg) was dissolved in dichloromethane (16 ml). The mixture was stirred under nitrogen at room temperature and diisopropylethylamine (2.11 ml) was added. The mixture was stirred and chloromethyl methyl ether (1.32 ml) was added dropwise. The mixture was stirred at room temperature, under nitrogen, for 18 hours and was then washed with water. The aqueous extracts were back-extracted with dichloromethane and the organic phases were combined, dried (MgSO$_4$) and the solvent evaporated under reduced pressure to give a yellow oil. This was subjected to silica gel chromatography (Merck Kieselgel 60, 30 g) using 5:1 petroleum ether (40°–60°):ethyl acetate as the eluting solvent. Fractions which contained the major component were combined and the solvent was evaporated under reduced pressure to give the *title compound* as a colourless oil (1.156 g), $^1$H n.m.r. (CDCl$_3$) δ1.94(2H), 2.36(1H), 3.36(3H), 3.40(3H), 3.48–3.62(2H), 3.92–4.10(2H), 4.5–4.84(6H), 4.93(1H), 7.25–7.40(5H).

INTERMEDIATE 12

(±)(1β,2α,3β,4α)-2-Fluoro-3-(methoxymethoxy)-4-[(methoxymethoxy)methyl]cyclopentanol Intermediate 11 (1.116 g) was dissolved in ethyl acetate (40 ml) and 2N hydrochloric acid (0.2 ml). 10%

Palladium on charcoal catalyst (225 mg) was added and the mixture was stirred and hydrogenated at room temperature and atmospheric pressure until uptake of hydrogen had ceased. The mixture was filtered through kieselguhr and the filter pad was washed with ethyl acetate. The washings and filtrate were combined and the solvent was evaporated under reduced pressure to give the *title compound* as a yellow oil. $\nu_{max}$ (CHBr$_3$) 3680, 3600, 3540, 1040 cm$^{-1}$. $^1$H n.m.r. (CDCl$_3$) δ1.93(2H), 2.39(1H), 3.38(3H), 3.40(3H), 3.45–3.62(2H), 4.03(1H), 4.27(1H), 4.6–4.9(5H).

INTERMEDIATE 13

(±)(1β,2α,3β,4α)-2-Fluoro-3-(methoxymethoxy)-4-[(methoxymethoxy)methyl]cyclopentanol, 4-methylbenzenesulphonate Intermediate 12 (205 mg) was dissolved in dichloromethane (5 ml). Triethylamine (0.2 ml) and 4-dimethylaminopyridine (126 mg) were added to the stirred solution, followed by p-toluenesulphonyl chloride (196 mg). The mixture was stirred at room temperature for 18 hours and was then loaded onto two Whatman PK6F preparative silica plates which were developed twice with 5:1 petroleum ether (40°–60°):ethyl acetate. The major component was eluted with ethyl acetate and the solvent was evaporated under reduced pressure to give the *title compound* (238 mg) as a pale yellow oil, $\nu_{max}$(CHBr$_3$) 3678, 1364, 1032 cm$^{-1}$. $^1$H n.m.r. (CDCl$_3$) δ 2.04(2H), 2.34(1H), 2.46(3H), 3.35(6H), 3.42–3.60(2H), 3.98(1H), 4.54–5.02(6H), 7.36(2H), 7.81(2H).

INTERMEDIATE 14

(±)(1'α,2'α,3'β,4'α)-2-Amino-6-chloro-9-[2-fluoro-3(methoxymethoxy)-4-[(methoxymethoxy)methyl]-1-cylcopentyl]-9H-purine Intermediate 13 (480 mg) was dissolved in dimethylsulphoxide (10 ml). Anhydrous potassium carbonate (254 mg) and 2-amino-6-chloropurine (250 mg) were added and the mixture was stirred at 80°, with exclusion of moisture, for 72 hours. The mixture was poured into brine and partitioned with ethyl acetate (100 ml). The organic extracts were dried (MgSO$_4$) and the solvent was evaporated under reduced pressure to give a yellow oil (398 mg). This was purified by preparative layer chromatography (Whatman PK6F silica plates) using ethyl acetate as the solvent. The polar uv-fluorescent quenching component was eluted with ethyl acetate to give the *title compound* as a pale yellow solid (74 mg), $\lambda_{max}^{MeOH}$ 222 nm (E$_1^1$, 740), 247.2 nm (E$_1^1$, 199), 309.8 nm (E$_1^1$, 227), $^1$H n.m.r. (DMSO-d$_6$) δ 2.12–2.50(3H), 3.31(3H), 3.33(3H), 3.52–3.68(2H), 4.06(1H), 4.55–5.0(5H), 5.10(1H), 7.0(2H), 8.24(1H).

INTERMEDIATE 15

(±)(1α,2β,3α,4α)-4-(2-Amino-6-chloro-9H-purin-9-yl)-3-fluoro-2-hydroxycyclopentanemethanol Concentrated hydrochloric acid (6.9 ml) was added dropwise to a stirred solution of Intermediate 6 (11 g) in a mixture of N,N-dimethylformamide (100 ml) and redistilled triethyl orthoformate (200 ml). After 3.5 h the solvents were removed in vacuo (oil pump) at 30° and the residual sticky foam was immediately dissolved in 0.6N hydrochloric acid (220 ml). After 30 min at room temperature the mixture was filtered and the red filtrate was concentrated on a rotary evaporator at 30° for a further 45 min during which time ca 75 ml of water was removed. The residual suspension was then adjusted to pH 7 with 6N sodium hydroxide solution and cooled in ice. The product was collected, washed with ice-water and dried in vacuo over P$_2$O$_5$ to provide the *title compound* as a cream solid (9.69 g). M.p. 200°–202°.

INTERMEDIATE 16

(±)(1'α,2'α,3'β,4'α)-5-Amino-1-[2-fluoro-3-hydroxy-4-(hydroxymethyl)cyclopentyl]-4-imidazolecarboxamide Ethyl N-(carbamoylcyanomethyl)formimidate (1.672 g) was added to a stirred solution of the hydrochloride salt of Intermediate 4 (2 g) and triethylamine (1.5 ml) in warm acetonitrile (30 ml) and the mixture was stirred and heated under reflux for 15 minutes. The solvent was evaporated and the residue was stirred with chloroform (4×50 ml). The resulting solid was recrystallised from ethanol to give the *title compound* as an off-white solid (477 mg). The mother liquors were stood in a refrigerator for 60 h and the resulting solid was collected by filtration and dried in vacuo at 70° to give a further crop of the *title compound* as an off-white solid (914 mg), m.p. 231°–232°.

INTERMEDIATE 17

(±)(1'α,2'α,3'β,4'α)-1-[2-Fluoro-3-hydroxy-4-(hydroxymethyl)cyclopentyl]-5-[[(benzoylamino)thiocarbonyl]amino]-4-imidazolecarboxamide Benzoyl isothiocyanate (889 mg) was added to a solution of Intermediate 16 (1.182 g) in ethanol (50 ml) and the mixture was heated under reflux for 24 h. The solution was concentrated to small volume and adsorbed onto silica gel (Merck Kieselgel 60, 10 g). This was placed on top of a silica gel chromatography column (Merck Kieselgel 60, 100 g) which was developed with chloroform-methanol mixtures. Fractions which contained the product were combined and the solvent was evaporated to give the *title compound* as a pale yellow foam (506 mg), $\lambda_{max}^{MeOH}$ 241.0 nm (E$_1^1$ 334), $^1$H n.m.r. (DMSO-d$_6$) δ 1.8–2.44 (3H), 3.38–3.64 (2H), 3.92 (1H), 4.4–4.68 (1H), 4.75 (1H), 4.68–5.0 (1H), 5.38 (1H), 7.09 (1H), 7.32 (1H), 7.56 (2H), 7.69 (1H), 7.8 (1H), 8.02 (2H).

EXAMPLE 1

(±)(1'α,2'α,3'β,4'α)-2-Amino-1,9-dihydro-9-[2-fluoro-3-hydroxy-4-(hydroxymethyl)cyclopentyl]-6H-purin-6-one Intermediate 6 (304 mg) was dissolved in dry N,N-dimethylformamide (4.2 ml). Triethyl orthoformate (7.395 g) and 12N hydrochloric acid (0.22 ml) were added and the resulting solution was kept at room temperature for 5 hours and was then stored in a refrigerator for 42 hours. The solution was concentrated in vacuo at 30° and the residual syrup was dissolved in 12N hydrochloric acid (42 ml). The resulting solution was heated under reflux for 5 hours and was then concentrated in vacuo at 50°. The concentrated solution was neutralised with 6N sodium hydroxide solution and the resulting solution was diluted with methanol and adsorbed onto silica gel. This silica gel was loaded onto the top of a silica gel chromatography column and the column was eluted with chloroform:methanol mixtures. Eluate which contained the product together with a more polar impurity were combined and the solvent was evaporated under reduced pressure to give a dark brown solid. This was dissolved in water and treated with charcoal. Removal of the charcoal by filtration through kieselguhr and evaporation of the filtrate under reduced pressure gave a gum-like solid. This was crystallised and recrystallised from water to give the *title compound* (49 mg). $\lambda_{max}^{H2O}$ 252.5 nm ($E_1^1$ 381), $\nu_{max}^{Nujol}$ 2500–3600, 1690, 1610 and 1580 cm$^{-1}$, $^1$H n.m.r. (DMSO-d$_6$) δ 1.90–2.46 (3H), 3.42–3.67 (2H), 4.01 (1H), 4.82 (1H), 4.79 (1H), 4.66–5.00 (1H), 5.46 (1H), 6.68 (2H), 7.71 (1H), 10.50 (1H).

EXAMPLE 2

Preparation of (i)

(+)(1'R,2'R,3'R,4'R)-2-Amino-1,9-dihydro-9-[2-fluoro-3-hydroxy-4-(hydroxymethyl)cyclopentyl]-6H-purin-6-one (ii)

(−)(1'S,2'S,3'S,4'S)-2-Amino-1,9-dihydro-9-[2-fluoro-3-hydroxy-4-(hydroxymethyl)cyclopentyl]-6H-purin-6-one Materials 5'-Nucleotidase (EC 3.1.3.5) from *Crotalus atrox* venom (Grade IV) and alkaline phosphatase type 7 s from bovine intestine were both obtained from Sigma Chemical Co Ltd, Fancy Road, Poole, Dorset, BH17 7 NH.

Herpes simplex type 1 thymidine kinase (TK) was obtained from HSV1 (strain HFEM) infected Vero cells. Cells were infected at 10 pfu/cell and at 18 hours post infection the infected cells were harvested and the TK purified by affinity chromatography as described by Fyfe et al., J. Biol. Chem., 1978, 253 8721–8727 and Cheng and Ostrander, J. Biol. Chem., 1976, 251, 2605–2610.

1. Thymidine kinase reaction: The 1 ml reaction mixture contained 50 mM Tris/HCl pH 7.5, 1 mg BSA, 5 mM ATP, 5 mM MgCl$_2$, 1 mM dithiothreitol, 10 mM phosphocreatine, 12.5 U creatine phosphotransferase and 2.5 mM NaF.
2. 5'-Nucleotidase reaction: The assay mixture contained 70 mM glycine pH 9.0 and 20 mM MgCl$_2$.
3. Alkaline phosphatase reaction: The assay mixture was the same as that for 5'-nucleotidase.

(a) Enzymatic synthesis of the 4-hydroxymethyl monophosphates of (±)(1'α,2'α,3'β,4'α)-2-Amino-1,9-dihydro-9-[2-fluoro-3-hydroxy-4-(hydroxymethyl)cyclopentyl]-6H-purin-6-one The compound of Example 1 (2 mg) was incubated with TK at 37° in the appropriate assay mixture. After 20 h the products of the reaction and the remaining substrate were extracted from the assay mixture as follows. Perchloric acid was added to a final concentration of 0.3M and the protein removed by centrifugation. To the supernatant an equal volume of 0.5M solution of tri-n-octylamine in 1,1,2-trichloro-1,2,2 trifluoroethane (1:5) was added and after gently mixing the phases were separated by low-speed centrifugation. The desired monophosphates and unreacted starting material remained in the aqueous layer, and were then separated by preparative ion exchange hplc using a Zorbax 10SAX column eluted in 0.4M ammonium acetate pH 4.3 and 10% methanol. The monophosphate mixture and nucleoside so obtained were freeze-dried separately. The nucleoside was then subjected to a further cycle of phsophorylation, and the resulting monophosphates purified as described. This process was carried out four times and the monophosphate products pooled for subsequent reaction.

(b)

(+)(1'R,2'R,3'R,4'R)-2-Amino-1,9-dihydro-9-[2-fluoro-3-hydroxy-4-(hydroxymethyl)cyclopentyl]-6H-purin-6-one The monophosphate mixture obtained in (a) was reacted with 5'-nucleotidase in the appropriate assay mixture (1 mg monophosphate/35 units of enzyme). After 15 minutes the product of the reaction and the remaining unreacted substrate were extracted from the assay mixture using the octylamine/trifluoroethane partition process described in (a) above and separated by preparative reverse phase hplc using a Zorbax ODS column. Sequential elution using 10 mM ammonium acetate pH 5.0 10% methanol/acetonitrile (1:1) followed by methanol/acetonitrile (1:1) yielded unreacted starting material followed by the *title compound* $[\alpha]_D^{20} = +48°$ (water).

(c)

(−)(1'S,2'S,3'S,4'S)-2-Amino-1,9-dihydro-9-[2-fluoro-3-hydroxy-4-(hydroxymethyl)cyclopentyl]-6H-purin-6-one The unreacted starting material left after the 5'-nucleotidase reaction (b) was degraded by the action of alkaline phosphatase for 15 minutes (1.3 mg of monophosphate to 2.85 units of enzyme). Extraction of the reaction mixture as described in (a) and purification by reverse phase preparative hplc as described in (b) gave the *title compound* $[\alpha]_D^{20} = -68°$ (water).

EXAMPLE 3

(±)(1'α,2'α,3'β,4'α)-2-Amino-1,9-dihydro-9-[2-fluoro-3-hydroxy-4-(hydroxymethyl)cyclopentyl]-6H-purin-6-one, hydrochloride salt Intermediate 15 (3 g) was heated under reflux in 1N hydrochloric acid (225 ml) for 4 h. The solution was concentrated under reduced pressure to give an orange syrup which was successively dissolved in water (3×40 ml) and re-evaporated to leave a yellow solid. Trituration with ethanol afforded the title compound as yellow crystals (2.47 g). A portion (200 mg) of this material was recrystallised from methanol to give the *title compound* as pale yellow crystals (48 mg). M.p. 257°–261°, $\lambda_{max}^{H2O}$ 252 nm ($E_1^1$ 413), $^1$H n.m.r. (DMSO-d$_6$) δ 11.97 (1H), 8.99 (1H), 7.25 (2H), 4.73–5.1 (3H), 4.02 (1H), 3.43–3.66 (2H) and 1.93–2.5 (3H).

Analysis found: C, 41.40; H, 4.80; N, 21.63; Cl, 11.1; C$_{11}$H$_{15}$ClFN$_5$O$_3$ (319.7) requires C, 41.31; H, 4.73; N, 21.9; Cl, 11.09%.

EXAMPLE 4

(±)(1'α,2'α,3'β,4'α)-2-Amino-1,9-dihydro-9-[2-fluoro-3-hydroxy-4-(hydroxymethyl)cyclopentyl]-6H-purin-6-one Intermediate 14 (61 mg) was suspended in 1N hydrochloric acid (2 ml) and the mixture was stirred and heated under reflux for 3 hours. The resulting solution was adjusted to pH 8 using 1N sodium hydroxide solution and was subjected to preparative high pressure liquid chromatography. The major fraction was evaporated under reduced pressure to give the *title compound* as a colourless solid (2 mg). N.m.r. analysis confirmed the product to be the same as that prepared in Example 1.

EXAMPLE 5

(±)(1'α,2'α,3'β,4'α)
2-Amino-1,9-dihydro-9-[2-fluoro-3-hydroxy-4-(hydroxymethyl)cyclopentyl]-6H-purin-6-one Intermediate 15 (2 g) was heated under reflux in 1N hydrochloric acid (150 ml) for 1 h. The solution was concentrated under reduced pressure at 40° to an orange syrup which was dissolved in ethanol (30 ml) and evaporated to give a yellow crystalline solid (2.1 g). This material was transferred to a sinter funnel and washed with ice-cold ethanol to leave a cream solid (1.86 g). This solid was suspended in water (20 ml) and the pH adjusted to 7 with 6N sodium hydroxide solution. The resulting suspension was heated on a steam bath to give a yellow solution which on cooling deposited fine needles. The crystals were collected, washed with ice-water and dried in vacuo over $P_2O_5$ at 100° for 4 h to give the *title compound* (1.48 g). A sample of this material was subjected to preparative HPLC and recrystallized from water to give the pure *title compound* (1.48 g), m.p. 266°–269° (softens at 217°) $\lambda_{max}^{H2O}$ 256 nm ($E_1^1$ 483), $^1$H n.m.r. (DMSO-$d_6$) δ 10.62 (1H), 7.74 (1H), 6.50 (2H), 5.42 (1H), 4.66–4.96 (3H), 3.91–4.09 (1H) and 1.9–2.4 (3H).

Analysis found: C, 42.82; N, 5.16; N, 23.04; $C_{11}H_{14}FN_5O_3.1.3H_2O$ requires C, 43.07; H, 5.45; N, 22.8%.

EXAMPLE 6

(±)(1'α,2'α,3'β,4'α)
2-Amino-1,9dihydro-9-[2-fluoro-3-hydroxy-4-(hydroxymethyl)cyclopentyl]-6H-purin-6-one, sodium salt 1M Sodium methoxide in methanol (1 ml) was added to a suspension of Example 1 (100 mg) in methanol (5 ml). Traces of insoluble material were removed by filtration. The filtrate, on standing for several days, deposited the *title compound* as white crystals (58 mg), m.p. 243°–250° (dec.), $\lambda_{max}^{H2O}$ 251 nm ($E_1^1$ 433), $^1$H n.m.r. (DMSO-$d_6$) δ 7.55 (1H), 6.86 (2H), 4.64–4.94 (2H), 3.98 (1H), 3.44–3.6 (2H) and 1.89–2.37 (3H).

EXAMPLE 7

(±)(1'α,2'α,3'β,4'α)-2-Amino-1,9-dihydro-9-[2-fluoro-3-hydroxy-4-(hydroxymethyl)cyclopentyl]-6H-purin-6-one Intermediate 17 (400 mg) was dissolved in 0.2M sodium hydroxide solution (12 ml). Iodomethane (0.2 ml) was added and the solution was stirred at room temperature for 90 minutes. Water (10 ml) was added and the solution was partitioned several times with ethyl acetate. The organic extracts were combined, dried (MgSO$_4$) and the solvent was evaporated to give a pale yellow solid (336 mg).

A portion (326 mg) of this solid was suspended in 0.880 aqueous ammonia (30 ml). The suspension was stirred and heated under reflux for 24 h. The resulting solution was evaporated and the resulting colourless solid was subjected to preparative high pressure liquid chromatography. A fraction which contained the required product was evaporated under reduced pressure to give the *title compound* (1 mg) as a colourless solid which was dried in vacuo at 70°. N.m.r. and u.v. analysis confirmed the product to be the same at that prepared in Example 1.

EXAMPLE 8

Pharmaceutical compositions (1) Topical creams

|  |  | % w/v |
|---|---|---|
| (a) | Active ingredient (as base) | 0.25 |
| (b) | Butylene glycol | 15.0 |
| (c) | Glycerol | 2.5 |
| (d) | Cetostearyl alcohol | 10.0 |
| (e) | Self emulsifying monostearin | 1.5 |
| (f) | Polyoxyethylene (2) oleyl ether | 5.0 |
| (g) | Beeswax | 3.0 |
| (h) | Chlorocresol | 0.1 |
|  | Distilled water to | 100.0 |

Heat the water to 70° and dissolve the chlorocresol (h). Melt (d), (e), (f) and (g) together, heating to −70°. Add the melt to the water with stirring. Disperse (a) in a mixture of (b) and (c) and add the dispersion (warmed to 55°) to the bulk mixture. Cool, with stirring, to 35°.

(2) Eye Ointment

|  | % w/v |
|---|---|
| Active ingredient (as base) | 3.0 |
| Liquid paraffin | 25.00 |
| White soft paraffin to | 100.0 |

Melt the white soft paraffin by heating to 70°. Disperse the active ingredient in the liquid paraffin, warm the dispersion to 55° and add it with stirring to the molten white soft paraffin. Cool, with stirring, to 35°.

(3) Eye Drops

|  | % w/v |
|---|---|
| Active ingredient | 1.0 |
| Benzalkonium chloride | 0.01 |
| Sodium chloride | 0.85 |
| Water for injections to 100.0 |  |

Dissolve the benzalkonium chloride, sodium chloride and active ingredient in the water. Filter the solution, collect the filtrate aseptically and fill (aseptically) into suitable sterile eye drop containers.

(4a) Oral Tablet

|  | mg/Tablet | % w/w |
|---|---|---|
| Active ingredient | equivalent to 100 mg base | 40.4 |
| Lactose | 100 mg | 37.0 |
| Maize starch | 50 | 18.5 |
| Polyvinyl pyrrolidone | 2 | 0.75 |
| Sodium starch glycolate | 7 | 2.6 |
| Magnesium stearate | 2 | 0.75 |

Sieve the active ingredient and maize starch through a 40 mesh screen. Blend the maize starch with the active ingredient in a suitable blender. Make an aqueous solution of the polyvinyl pyrrolidone in a 5–10% w/v solution. Add this solution to the mixing powders and mix until granulated. Using suitable equipment pass the granulate through a 12 mesh screen. Dry the granules in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine. The tablets may be covered in a thin polymer coat applied by the usual film coating techniques. A pigment may be included in the film coat.

(4b) Oral Tablet

|  | mg/tablet | % w/w |
|---|---|---|
| Active Ingredient | equivalent to 100 mg base | 36.3 |
| Microcrystalline cellulose | 183 mg | 61.0 |
| Sodium starch glycolate | 6 mg | 2.0 |
| Magnesium stearate | 2 mg | 0.7 |

Sieve the active ingredient and the microcrystalline cellulose through a 40 mesh screen. Sieve the sodium starch glycolate and magnesium stearate through a 60 mesh screen. Blend the powders together in a suitable blender until homogenous. Compress on appropriate punches on an automatic tablet machine. The tablets may be covered in a thin polymer coat applied by the usual film coating techniques. A pigment may be included in the film coat.

(5) Oral Capsule

|  | mg/Capsule | % w/w |
|---|---|---|
| Active ingredient | equivalent to 100 mg base | 43.6 |
| Lactose anhydrous | 126 mg | 50.4 |
| Magnesium stearate | 2 mg | 0.8 |
| Sodium starch glycolate | 13 mg | 5.2 |

Sieve all the ingredients and mix in a suitable blender. Fill into suitable size hard gelatin capsules using an automatic capsule filling machine.

(6) Oral syrup

|  | % w/v |
|---|---|
| Active ingredient (as base) | 1.0 |
| Sucrose | 60.0 |
| Distilled water to | 100.00 |

Dissolve the active ingredient and sucrose in part of the water and then make to volume. Fill the solution into suitable syrup containers.

(7) Oral suspension

|  | % w/v |
|---|---|
| Active ingredient (as base) | 5.0 |
| Sorbitan mono-oleate | 1.0 |
| Sucrose | 50.0 |
| Carboxymethyl cellulose | 5.0 |
| Distilled water to | 100.0 |

Disperse the carboxymethyl cellulose in part of the water with stirring. Dissolve the sorbitan mono-oleate and sucrose in the dispersion, with stirring. Disperse the active ingredient in the resultant mixture. Make the mixture to volume and fill into suitable suspension containers.

(8) Powder

|  | % w/v |
|---|---|
| Active ingredient (as base) | 3.0 |
| Maize starch to | 100.00 |

Blend the active ingredient and the maize starch in a suitable mechanical blender. Fill the resultant powder blend into suitable powder containers.

In the above pharmaceutical examples the active ingredient is (±)(1'α,2'α,3'β,4'α)-2-amino-1,9-dihydro-9-[2-fluoro-3-hydroxy-4-(hydroxymethyl)cyclopentyl]-6H-purin-6-one in the form of its hydrochloride salt unless otherwise stated. Other compounds of the invention may be formulated in a similar manner.

We claim:
1. A compound of formula (I)

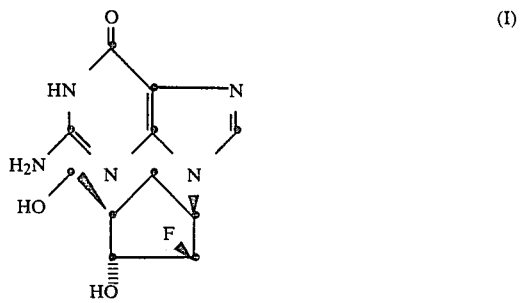

and physiologically acceptable salts and solvates thereof.

2. The compound of claim 1 which is (±)(1'α,2'α, 3'β, 4'α)-2-amino-1,9-dihydro-9-[2-fluoro-3-hydroxy-4-(hydroxymethyl)cyclopentyl]-6H-purin-6-one and physiologically acceptable salts and solvates thereof.

3. The compound of claim 1 which is (+)(1'R,2'R,3'R,4'R)-2-amino-1,9-dihydro-9-[2-fluoro-3-hydroxy-4-(hydroxymethyl)cyclopentyl]-6H-purin-6one and physiologically acceptable salts and solvates thereof.

4. A method for the therapy or prophylaxis of Herpetoviridae infections in a human or animal subject which comprises administering an effective amount of a compound of formula (I) as defined in claim 1 or a physiologically acceptable salt or solvate thereof.

5. Pharmaceutical compositions for the therapy or prophylaxis of Herpetoviridae infections in a human or animal subject comprising a therapeutically or prophylactically effective amount of at least one compound of formula (I) as defined in claim 1 or a physiologically acceptable salt or solvate thereof in association with one or more pharmaceutical carriers or excipients adapted for use in human or veterinary medicine.

6. Compositions as claimed in claim 5 formulated for oral, buccal, parenteral, topical or rectal administration.

7. Compositions as claimed in claim 6 for oral administration in a form selected from the group consisting of tablets, capsules, syrups and suspensions.

8. Compositions as claimed in claim 6 for topical administration in a form selected from the group consisting of ointments, creams, lotions, powders, pessaries, sprays, aerosols and drops.

9. The 4-hydroxymethyl monophosphates of the (+) and (−) enantiomers of the compound of formula (I) as defined in claim 1.

* * * * *